United States Patent [19]

Finkelstein et al.

[11] Patent Number: 4,583,564
[45] Date of Patent: Apr. 22, 1986

[54] DENTAL FLOSS

[75] Inventors: Paul Finkelstein, Princeton Junction; Kevin G. Yost, Short Hills, both of N.J.

[73] Assignee: Johnson & Johnson Products, Inc., New Brunswick, N.J.

[21] Appl. No.: 749,595

[22] Filed: Jun. 27, 1985

[51] Int. Cl.⁴ ............................................. A61C 15/00
[52] U.S. Cl. ..................................................... 132/91
[58] Field of Search ............................. 132/91, 93, 89; 425/129, 111; 264/157

[56] References Cited

U.S. PATENT DOCUMENTS

| | | | |
|---|---|---|---|
| 2,667,443 | 1/1954 | Ashton | 132/91 X |
| 2,981,264 | 4/1961 | DeFelice | 132/91 |
| 3,930,059 | 12/1975 | Wells | 132/91 |
| 3,942,539 | 3/1976 | Corliss | 132/91 |
| 4,029,453 | 6/1977 | Campron, Jr. | 132/91 |

*Primary Examiner*—Gregory E. McNeill
*Attorney, Agent, or Firm*—Steven P. Berman

[57] ABSTRACT

A dental floss consisting of filaments containing a higher melting point core material and a lower melting point sheath material whereby the sheath material fibers are fused by subjecting them to a sufficient temperature to achieve same.

7 Claims, No Drawings

DENTAL FLOSS

BACKGROUND OF THE INVENTION

This invention relates to articles for cleaning the interproximal surfaces of the teeth and more particularly to dental floss. It has been shown that tooth decay and dental disease can be attributed to bacterial action resulting from the formation of plaque about the teeth and/or the entrapment of food particles between the teeth. The removal of plaque and entrapped food particles reduces caries, reduces the tendency towards gingivitis, and reduces mouth odor as well as generally improving oral hygiene. Conventional brushing of the teeth has been found to be unsatisfactory to effect the removal of entrapped food particles from some crevices between the teeth and/or to effectively remove the interproximal plaque. To supplement brushing, various materials have been used to clean the interproximal spaces and surfaces of the teeth, for example, dental floss.

Dental floss is available in either a waxed or unwaxed variety. Waxed dental floss is generally comprised of multifilament yarns coated with a white or colorless wax usually having a melting point of from about 140° F. to 200° F. Some people have the unsubstantiated belief that flossing with a waxed floss may leave residues of wax on the teeth which may be harmful whereas others merely do not like the waxy sensation in their mouths. Unwaxed dental floss is generally composed of multifilament yarns twisted together and coated with a non-wax bonding material. While satisfactory for many users, such floss does present problems for some who find it difficult to insert the floss in tight spaces between the teeth. This is due in part to the inability of the various filaments to easily slide over one another as the floss is forced between contacting teeth as well as in part due to the non-wax coating utilized. The sliding of the filaments over the tooth surface and over one another is inhibited by the nature of the materials from which commercially available floss products are made. These include a plurality of individual filaments of substances such as nylon 6, nylon 6,6, rayon, polyester, acetate polymers, polypropylene and similar plied multifilament yarns as well as cotton, wool and other staple yarns.

SUMMARY OF THE INVENTION

It is an object of this invention to provide an improved dental floss.

It is a further object of this invention to provide a dental floss allowing easier insertion into tight spaces between the teeth.

It is a still further object of this invention to provide a dental floss without a wax coating or non-wax binder.

These and other objects of the present invention will be set forth in, or apparent from, the following detailed description of the invention.

The foregoing objects and other features and advantages of the present invention are achieved by a dental floss which is a bicomponent, multifilament dental floss.

DESCRIPTION OF PREFERRED EMBODIMENTS

The bicomponent, multifilament dental floss of the present invention comprises a dental floss wherein each filament is composed of a high melting point core material and a lower melting point sheath material.

The core material can be any suitable floss material having a higher melting point than the sheath material. Some suitable materials for the core material are polyester, nylon 6, nylon 6,6 and the like. The sheath material can be any suitable floss material having a lower melting point than the core material. The sheath material selected should preferably be one which aids passage between the teeth, such as polyethylene, polypropylene and the like. If desired, one can also utilize different types of the same polymeric materials as both the core material and sheath material, provided that the melting point of the sheath material is at least about 100° F. less than the melting point of the core material.

The bicomponent filament can be made by extruding the two different polymers, i.e., the core material and the sheath material from two separate extruders through a compound die. The ratio of core material to sheath material can be from about 90%/10% to about 20%/80% with a 50 %/50% ratio preferred. From about 25 to 1000 of the individual filaments, preferably about 55 to 450 filaments are formed together into a yarn of sufficiently small diameter to permit insertion into the interproximal areas between closely contacting teeth. If desired, the filaments can be colored by placing a suitable pigment, such as naphthol red, phthalocyanine green, diarylide yellow or the like in the polymer melt prior to extrusion of the filaments.

It is common practice to twist the individual filaments forming the yarn in order to give the floss additional integrity, that is additional strength to prevent filament separation and shredding. The twist incorporated into the yarn should be enough to aid handling and keep the filaments together during use, but should not be so great that the floss becomes stiff and inflexible. The twist of the yarn can be from about 0 to 6 turns per inch, with a preferred twist of from about 0.5 to 2.5 turns per inch. Other techniques to give additional integrity to the floss can also be utilized, including false twist, air-jet entanglement and the like.

The tensile strength of the finished floss should be between 3 and 25 pounds, although higher tensile strengths are acceptable. The preferred tensile strength is about 6 to 20 pounds. A finished yarn of less than 4 pounds will tend to break easily during use and would be unacceptable for a dental floss, and a finished yarn of more than 25 pounds tensile strength offers no advantages yet is less economical to manufacture. The yarn may be of 200 to 2000 denier, while the preferred dental floss is of 400 to 900 denier for proper hand feel and comfortable use in the mouth.

Whereas other flosses receive a wax or non-wax coating, the outer fibers of this invention are held together by fiber-to-fiber fusion. This fusion is achieved among the outer filaments by short duration exposure to heat at a temperature sufficient to soften the lower melting point sheath material but insufficient to affect the higher melting point core material. The amount of fusion should be enough to, in effect, create a shell on the outside of the floss, without fusing the entire yarn bundle. If the latter occurs, the floss becomes stiff and unacceptable.

A method of preparing the dental floss of the present invention is as follows: appropriate materials are selected, for example, as the sheath material, Fortiflex high density polyethylene T60-4200-119 available from Soltex and as the core material, Carodel C-1000 polyester available from Rohm & Haas. These materials are extruded from two separate extruders through a compound die such that each filament has a core to sheath ratio of about 1:1.

The filaments are drawn into a yarn to provide a final yarn of about 900 denier and, if desired at this point, a finishing aid can be added to aid in handling the yarn. The yarn is then given two turns per inch of twist on a suitable twist apparatus. The twisted yarn is then passed through a heat apparatus at a temperature of about 170° C. for about 5 seconds to fuse the outside of the floss. The finished product is then wound on large spools to be packaged as desired.

A dental floss as described herein is perceived effective in cleaning between the teeth and exhibits ease of insertion between the teeth as well as ease of handling. The dental floss of this invention is also judged to be of the right flexibility, softness and gentleness to the gums. Furthermore, by not having a wax or non-wax coating, the resulting floss is deemed easier to use and is less costly to manufacture.

In order to demonstrate the ease of insertion of the dental floss of the present invention between tightly contacting teeth, the following experiment was carried out to measure the force required to pass the floss between two contact points in a specially constructed apparatus. This apparatus consists of two plastics arms, each 1″ by 0.5″ by 8″, fastened into a block at one end to hold the arms 0.625″ apart with the 1″ sides towards each other. The arms rounded on the end opposite to the block to avoid catching the floss. A sliding collar with set screws fits around the arms allowing adjustment of the force required to move the arms apart. At 1.125″ from the end opposite the mounting block, holes are placed through both arms for the shafts of steel contact points. One contact point consists of a hemisphere with a 0.3125″ diameter, thus extending half the distance between the two arms. The second contact point is cone shaped, also with a height of 0.3125″. It thus extends from its arm half the distance to the other arm and just touches the hemisphere. These two contact points simulate two closely contacting teeth.

The floss to be tested is mounted in a U-shaped frame and is held securely with screws and washers, so the floss can be moved up to and between the contact points perpendicular to the plastic arms. Both the U-shaped frame and the block holding the plastic arms include the necessary holes for mounting to equipment for measuring force. To perform the test, the collar is set along the arms to adjust the tightness of the contact points. The floss is passed between the points and the force required for the passage is measured.

Five commercially available unwaxed dental flosses were tested by passing a sample of each between the contact points and the force required for the passage was measured. The test was also run with a dental floss prepared according to the teachings of the present invention.

The test was conducted at three settings of the adjustable collar to simulate a range of tightness of teeth. The forces required to pass the dental floss between the contact points is measured in pounds and the results are shown in Table I below wherein each mean and the standard deviation in parentheses represent five readings.

TABLE I

| Commercial | Setting of Adjustable Collar | | |
|---|---|---|---|
| Floss # | 3.5″ | 3.0″ | 2.5″ |
| 1 | 2.366 (0.072) | 3.632 (0.052) | 4.983 (0.219) |
| 2 | 2.239 (0.042) | 3.497 (0.060) | 4.640 (0.168) |
| 3 | 2.280 (0.069) | 3.344 (0.065) | 4.553 (0.097) |
| 4 | 2.150 (0.014) | 3.168 (0.057) | 4.357 (0.081) |
| 5 | 2.312 (0.066) | 3.429 (0.158) | 4.528 (0.112) |
| Floss of Present Invention | 1.653 (0.021) | 2.434 (0.034) | 3.322 (0.032) |

The results of the above tests clearly show that the dental floss of the present invention requires statistically significantly less force to pass between the contact points than the commercially available dental flosses.

In addition to the preferred embodiments described herein, other arrangements and variations within the spirit of the invention and the scope of the appended claims will occur to those skilled in the art.

What is claimed is:

1. A dental floss comprising filaments containing a higher melting point core material and a lower melting point sheath material whereby the filaments are subjected to a temperature sufficient to achieve fiber to fiber fusion of the sheath material fibers.

2. The floss of claim 1 wherein the core material is selected from the group consisting of polyester, nylon 6, and nylon 6,6.

3. The floss of claim 2 wherein the core material is polyester.

4. The floss of claim 1, wherein the sheath material is selected from the group consisting of polyethylene, polypropylene and polyester.

5. The floss of claim 4 wherein the sheath material is polyethylene.

6. The floss of claim 1 wherein said floss contains from about 25 to 1000 filaments.

7. The floss of claim 1 wherein said floss has a twist of from about 0 to 6 turns per inch.

* * * * *